(12) United States Patent
Payen De La Garanderie et al.

(10) Patent No.: US 8,283,131 B2
(45) Date of Patent: Oct. 9, 2012

(54) METHODS AND KITS FOR THE RAPID DETERMINATION OF PATIENTS AT HIGH RISK OF DEATH DURING SEVERE SEPSIS AND SEPTIC SHOCK

(75) Inventors: Didier Payen De La Garanderie, Paris (FR); Anne-Claire Lukaszewicz, Chantilly (FR)

(73) Assignee: Assistance Publique-Hopitaux de Paris, Paris (FR)

( * ) Notice: Subject to any disclaimer, the term of this patent is extended or adjusted under 35 U.S.C. 154(b) by 500 days.

(21) Appl. No.: 12/259,596

(22) Filed: Oct. 28, 2008

(65) Prior Publication Data

US 2010/0105084 A1 Apr. 29, 2010

(51) Int. Cl.
*G01N 33/53* (2006.01)
*G01N 33/533* (2006.01)
*G01N 33/535* (2006.01)
*G01N 33/536* (2006.01)
*G01N 33/543* (2006.01)
*C07K 16/24* (2006.01)

(52) U.S. Cl. ........ 435/7.92; 435/7.1; 435/7.24; 435/7.8; 435/7.94; 435/975; 436/501; 436/518; 436/536; 436/547; 436/172; 436/811; 530/388.23; 530/388.25; 530/388.7; 530/389.2; 530/389.3; 530/389.6; 530/391.1; 530/391.3; 424/9.2

(58) Field of Classification Search ............... 435/6, 7.1, 435/7.24, 7.8, 7.92, 7.94, 975; 436/501, 436/518, 536, 547, 811, 172; 530/388.23, 530/388.25, 388.7, 389.2, 389.3, 389.6, 391.1, 530/391.3; 424/9.2; 514/921

See application file for complete search history.

(56) References Cited

U.S. PATENT DOCUMENTS

| | | | |
|---|---|---|---|
| 5,270,163 A | 12/1993 | Gold et al. | |
| 2005/0288211 A1* | 12/2005 | Tessier et al. | 514/2 |
| 2006/0035221 A1 | 2/2006 | Bergmann et al. | |
| 2006/0234295 A1* | 10/2006 | Bergmann et al. | 435/7.1 |

FOREIGN PATENT DOCUMENTS

| | | |
|---|---|---|
| EP | 1 950 310 A1 | 7/2008 |
| EP | 2 085 486 A1 | 8/2009 |
| WO | WO 2008/104321 A1 | 9/2008 |

OTHER PUBLICATIONS

Ikemoto et al., 2003. New ELISA system for myeloid-related protein complex (MRP8/14) and its clinical significance as a sensitive marker for inflammatory responses associated with transplant rejection. Clinical Chemistry 49: 594-600.*
Payen et al., 2008. Gene profiling in human blood leucocytes during recovery from septic shock. Intensive Care Medicine 34:1371-1376.*
O'Reilly et al., 1999. Endotoxin, sepsis, and the primrose path. Shock 12: 411-420.*
Roth et al., 1992. Complex pattern of the myelo-monocytic differentiation antigens MRP8 and MRP14 during chronic airway. Immunobiology 186: 304-314.*
Vogl et al., 2007. Mrp8 and Mrp14 are endogenous activators of Toll-like receptor 4, promoting lethal, endotoxin-induced shock. Nature Medicine 13: 1042-1049.*
Foell et al., 2004. Phagocyte-specific calcium-binding S100 proteins as clinical laboratory markers of inflammation. Clinica Chimica Acta 344: 37-51.*
Vandal et al., 2003. Blockade of S100A8 and S100A9 suppresses neutrophil migration in response to lipopolysaccharide. Journal of Immunology 171: 2602-2609.*
International Search Report for International Application No. PCT/IB2009/007493, mailed Feb. 26, 2010.
International Preliminary Report on Patentability for International Application No. PCT/IB2009/007493, issued May 3, 2011.
Clec'h, C., Ferriere, F., Karoubi, P., Fosse, J.P., Cupa, M., Hoang, P. and Cohen, Y. (2004) Diagnostic and prognostic value of procalcitonin in patients with septic shock. Crit Care Med, 32, 1166-1169.
Levy, M.M., et al.; "The Surviving Sepsis Campaign: Results of an international guideline-based performance improvement program targeting severe sepsis"; Critical Care Medicine; Feb. 2010; Vol. 38, Issue 2; pp. 367-374.

* cited by examiner

*Primary Examiner* — Gail R Gabel
*Assistant Examiner* — James L Grun
(74) *Attorney, Agent, or Firm* — Alston & Bird LLP

(57) ABSTRACT

The present invention provides for the in vitro establishing of a prognosis for a subject in severe sepsis with at least two organ failures or in septic shock with at least two organ failures. Embodiments of the invention comprise the steps of measuring the level of the S100A8/A9 complex from a biological sample from a subject, and comparing the measured level to a predetermined threshold in which the measured level of the S100A8/A9 complex above the predetermined threshold is indicative of a bad prognosis and a measured level of the S100A8/A9 complex below the predetermined threshold is indicative of a good prognosis.

5 Claims, 3 Drawing Sheets

METHODS AND KITS FOR THE RAPID DETERMINATION OF PATIENTS AT HIGH RISK OF DEATH DURING SEVERE SEPSIS AND SEPTIC SHOCK

FIELD OF THE INVENTION

The present invention relates to the field of treatment of serious medical syndromes such as severe sepsis or septic shock. In particular, the present invention provides methods and kits to obtain an early evaluation of mortality risk and help therapeutic decisions for patients in severe sepsis with two organ failures, for example for patients in septic shock.

BACKGROUND AND PRIOR ART

Septic shock is the most severe clinical presentation of sepsis, with a poor prognosis despite intensive therapeutic support and anti-infectious strategy to eradicate the infection foci. The sepsis syndrome is defined as symptoms related to the host response to abnormal presence of micro-organisms or their antigenic fractions. The local infection might spread out for different reasons to the whole body, with a particular activation of blood immune cells controlling the innate immunity during the early phase and activation of the adaptive immunity in a second time. Such an intense immune activation in blood may in turn target organs that were not initially concerned by the initial infection, leading to immune toxicity and dysfunction of these organs. The high mortality rate of septic shock (around 50%) results from a combination of organ failures, comorbidities and virulence of micro-organisms. Death may occur at different times of evolution, most often during the first week despite intensive resuscitation.

A number of studies examining therapeutic interventions have generated important but controversial results, such as the use of corticosteroids (Annane et al., 2002; Sprung et al., 2008), activated protein C (Bernard et al., 2001), and tight glycaemic control (van den Berghe et al., 2001). The absence of an early, specific and sensitive marker for determining prognosis thus creates difficulties not only for clinicians with regard to prescription of expensive drugs and futile maintenance of life support, but also for trial investigators with regard to the selection of patients for study inclusion. Some promising markers have been tested, such as procalcitonin (Clec'h et al., 2004), HLA-DR (Monneret et al., 2006), IL-6 (Abraham et al., 2001), and soluble triggering receptor expressed on myeloid cells-1 (sTREM) (Gibot et al., 2005); but results are conflicting.

Recently, a novel group of molecules—known variously as "endokines", "alarmins" or "damage-associated molecular pattern proteins (DAMPs)"—that are released by activated or damaged cells under conditions of cell stress has been investigated (Oppenheim et al., 2007). Among these, phagocytic S100 proteins, members of the calgranulin family that mediate inflammatory responses (Vogl et al., 2007) and organ function (Boyd et al., 2008) appear to be of importance in sepsis. An emerging concept of pattern recognition involves the multi-ligand receptor for advanced glycation end products (RAGE) and Toll-like receptors (TLRs) in sensing not only pathogen-associated molecular patterns (PAMPs) but also endogenous DAMPs, including the S100 proteins (Brunn and Platt, 2006; Foell et al., 2007).

Overexpression of the genes of S100A8 and A9 has been shown in mice submitted to lipopolysaccharide (LPS) or caecal ligation and puncture (CLP) challenge (Vogl et al., 2007), in cardiomyocytes incubated with LPS (Boyd et al., 2008), in kidney tissue after ischaemia/reperfusion (Grigoryev et al., 2008), in healthy volunteer leucocytes after LPS injection (Talwar et al., 2006) and in septic shock patients (Payen et al., 2008). Since S100A8 and S100A9 proteins are found in both intracellular and extracellular spaces, they could potentially act both within the cell and in an autocrine or paracrine manner. In mice with septic shock, there were high levels of both gene expression and the proteins (Vogl et al., 2007). Few studies have examined cellular or extracellular levels of these proteins in human septic shock.

SUMMARY OF THE INVENTION

Recently, the inventors found a close correlation between the evolution of S100A8 and A9 gene expression and the plasma level of the S100A8/A9 complex during the recovery phase of human septic shock (Payen et al., 2008), incorporated herein by reference.

The experimental part below reports the results of a further investigation in patients with septic shock examining gene expression of S100A8 and A9 and plasma levels of the S100A8/A9 complex at day 0 after occurrence of the second organ failure. In this multicentre study, the inventors found a large difference in the plasma S100A8/A9 complex level between eventual survivors and non-survivors, with a specificity and sensitivity of 100%. The threshold for risk of death was determined as 8.1 µg/ml.

DETAILED DESCRIPTION OF THE PREFERRED EMBODIMENTS

Figure 1:
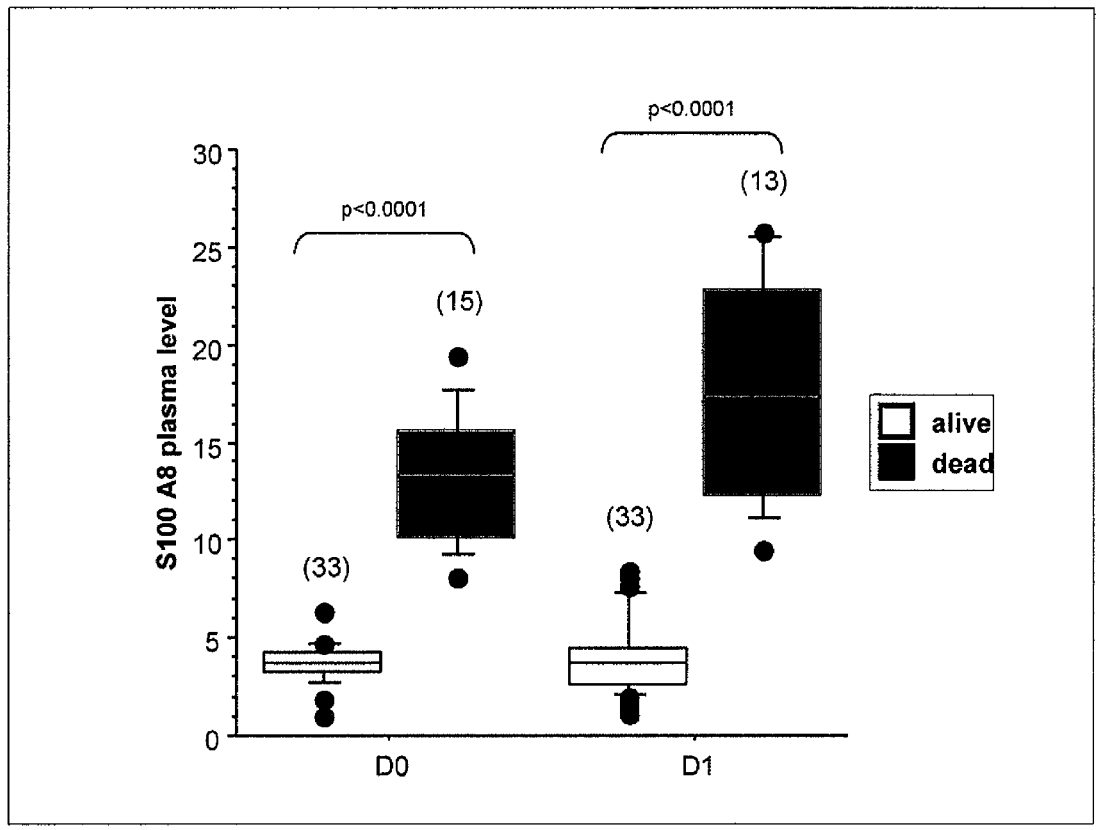
FIG. 1: shows the plasma level of the complex S100 A8/A9 at day 0 and day 1 of the survivors (white box) and non survivors (black box) septic shock patients. Box plot represents the median with the 25 and 75 percentiles, the bar corresponded to the 10th and 90th percentiles. Dots are the values lower than 10th percentile or over the 90th percentile. Statistics were performed with Mann Whitney non parametric test.

In the present text, the terms "sepsis", "severe sepsis" and "septic shock" are to be understood according to the definitions established in 1991 by the American College of Chest Physicians (ACCP) and the Society of Critical Care Medicine (SCCM) and confirmed in 2001 (Levy et al., 2003). These and other definitions used herein are summarized below:

A "sepsis" is a systemic inflammation in response to infection.

A "severe sepsis" is defined as a sepsis with at least one organ dysfunction.

Among severe sepsis syndromes, the most severe cases exhibit two organ failures or even more. Although not very common, some severe sepsis cases with two organ dysfunctions distinct from acute respiratory failure are observed: this kind of cases are defined as "severe sepsis with at least two organ failures", and are distinct from septic shocks.

A "septic shock" is defined as a sepsis with acute circulatory failure.

An "acute circulatory failure" is a persistent arterial hypotension (systolic arterial pressure<90 mm Hg, a MAP<60 mmHg or a reduction in systolic blood pressure of >40 mm Hg from baseline) despite adequate volume resuscitation, in the absence of other causes for hypotension.

A "septic shock with at least two organ failures" is a septic shock with at least one organ failure (e.g., kidney, liver, . . . ) in addition to the acute circulatory failure.

In the present text, patients who are considered are those, either in severe sepsis or in septic shock, but in both cases with at least two organ failures. For these patients, "day 0" designates the 24-hours period after the onset of the second organ failure.

Other definitions will be specified below, when necessary.

A first aspect of the present invention is a method for in vitro establishing a prognosis for a subject in severe sepsis with at least two organ failures, or for a subject in septic shock with at least two organ failures, comprising the following steps:

(i) from a biological sample from said subject, measuring the level of the S100A8/A9 complex, (ii) comparing said level to a predetermined threshold, wherein a level of the S100A8/A9 complex above said predetermined threshold is indicative of a bad prognosis and a level of the S100A8/A9 complex below said predetermined threshold is indicative of a good prognosis.

According to a preferred embodiment of this method, the method said biological sample used in step (i) has been collected at day 0, day 1 or day 2 after the onset of the second organ failure. In an even more preferred embodiment, the biological sample has been collected at day 0. This biological sample can be, for example, selected amongst plasma, saliva, urine, cerebrospinal fluid, pleural fluid and peritoneal fluid.

The threshold to be considered when performing the above method is predetermined by measuring the level of the S100A8/A9 complex in a representative cohort of individuals having undergone a severe sepsis or septic shock with at least two organ failures, and for whom the outcome is known. The threshold is calculated to obtain the best predictability (sensitivity and specificity) for the risk of death. For example, when the level of the S100A8/A9 complex is measured in the plasma with a technology similar to that described in the experimental part, a predetermined threshold of 7 to 9 µg/ml, preferably from 7.8 to 8.3 µg/ml and for example 8.1 µg/ml, can be considered. On the cohort used in the present study, the level of S100A8/A9 complex led to a sensitivity and a specificity of prognosis (risk of death) of 100%, considering this threshold. Of course, the skilled artisan is free to re-evaluate this threshold on a larger cohort of patients, and by using any kind of technology for measuring the S100A8/A9 complex level.

In a preferred embodiment, the measure performed in step (i) is done by an immunoassay, for example with an antibody which specifically binds to the S100A8/A9 complex. Several examples of antibodies specifically binding to S100A8/A9 complex (also referred to as MRP8/14 complex) have already been described in the literature, for example by Ikemoto et al. (Ikemoto et al., 2003). Of course, alternative techniques can be used to quantify the S100A8/A9 complex in said biological sample, such as, for example, the technique described by Roth et al. (Roth et al., 1993). The skilled artisan can also use, instead of antibodies specific for the S100A8/A9 complex, any other molecule specifically binding to said complex, such as, for example, antibody fragments or specifically designed aptamers. Aptamers are single stranded nucleic acid molecules (DNA or RNA) that are selected in vitro for their ability to bind to a target molecule; this selection can be performed, for example, by the SELEX method (Systematic Evolution of Ligands by Exponential Enrichment) described in U.S. Pat. No. 5,270,163. Besides, the crystal structure of the human S100A8/A9 complex can be used by the skilled artisan for obtaining molecules specifically binding to said complex (Komdorfer et al., 2007).

In a particular embodiment of the method according to the present invention, the immunoassay performed is an ELISA assay such as described in the experimental part below. Alternatively, fluorescently labeled antibodies can be used, for example for performing flux cytometry. Of course, the skilled artisan can choose any other immunoassay for performing a method according to the present invention.

If necessary, the skilled artisan can combine several markers for establishing a prognosis in cases of sepsis or septic shock with at least two organ failures. Amongst the markers which can be used in combination with S100A8/A9 complex concentration, procalcitonin (PCT), N-terminal pro-brain natriuretic peptide (BNP), soluble triggering receptor expressed on myeloid cells-1 (sTREM), IL-6 and sRAGE can be cited, as well as the sepsis related organ failure (SOFA) score, the HLA-DR level on circulating monocytes, SAPS II score, etc. The present invention hence also pertains to a method as described above, further comprising a step of measuring the level of at least one other species in a biological sample from said patient (the same biological sample as that in which S100A8/A9 complex concentration is measured, or another biological sample if appropriate), and a step of comparing said level to a predetermined threshold. By "species" is herein understood any component, molecule or complex, which can be used as a marker. In a particular embodiment, said other species is/are measure in the same biological sample as S100A8/A9 complex, and is/are selected amongst procalcitonin (PCT), N-terminal pro-brain natriuretic peptide (BNP), soluble triggering receptor expressed on myeloid cells-1 (sTREM), IL-6 and sRAGE.

According to another aspect of the present invention, the invention concerns a method for performing a follow-up of a patient in severe sepsis with at least two organ failures or in septic shock with at least two organ failures, by measuring the evolution of the plasma level of S100A8/A9 complex in said patient, wherein a decrease in said level indicates that said patient is recovering. According to this method, if a patient had a level of S100A8/A9 complex at D0 above the predetermined threshold defined above, and if said level remains above the threshold, this indicates that the patient has a great probability of death.

Another method according to the present invention aims at performing a follow-up of a patient in severe sepsis or in septic shock with at least two organ failures, by measuring the evolution of the expression level of S100A8 and/or S100A9 in said patient, wherein a decrease in said level indicates that said patient is recovering. This method is illustrated by the publication of D. Payen et al., incorporated herein by reference (Payen et al., 2008). When performing this method, the expression level of S100A8 and/or S100A9 will preferably be measured by quantitative amplification, for example by quantitative RT-PCR as described in Payen et al., supra.

In the above-described follow-up methods, the measures (of the S100A8/A9 complex or of the expression of S100A8 or S100A9) are performed on biological samples obtained from said patient at several time points after admission, for example each day during the first week and then, depending on the clinical context, at the same frequency or at a lower frequency.

According to yet another aspect, the present invention pertains to a method for helping decision for treatment withdrawal for a patient in severe sepsis with at least two organ failures or in septic shock with at least two organ failures, comprising the following steps:

(i) establishing a prognosis for said patient, by a method according to claim 1 (as soon as possible after the onset of the second organ failure);

(ii) measuring the level of S100A8/A9 complex in a biological sample from said patient, obtained after several days (e.g., 2 weeks) of treatment;

wherein if no decrease in the level of S100A8/A9 complex is observed and if the clinical status remains severe, treatment withdrawal is decided. When performing this method, the physician will consider that the clinical status remains severe if the patient still has tow organ failures or more. Treatment withdrawal will in particular be decided if the S100A8/A9 complex level measured in step (i) was above the above-defined threshold and remains above this threshold after several days of treatment.

Since the present invention provides a reliable prognosis marker for patients in very severe conditions (i.e., in severe sepsis with at least two organ failures or in septic shock with at least two organ failures), this prognosis marker can be used to better select the individuals to be enrolled in clinical trials for testing new treatments aiming at improving either the duration of intensive support before the patient leaves the intensive care unit or the outcome of these pathologies.

In the first case, the patients who will be enrolled are those with a good prognosis, in order to avoid noise related to "desperate" patients. The invention hence also pertains to a method for determining if a subject in a very severe condition with at least two organ failures is to be enrolled in a clinical trial for evaluating the efficiency of a pharmaceutical treatment for shortening the need of intensive support for such patient, wherein said method comprises a step of establishing a prognosis for said subject by a method as described above, and wherein said patient is enrolled if the measured level of S100A8/A9 complex is below the predetermined threshold.

To the contrary, patients with a bad prognosis will be enrolled in trials for evaluating new treatments for improving outcome of very severe conditions with at least two organ failures, so that a drug with potential severe side-effects will not be given to patients supposed to recover by "classical" resuscitation, and so that the results be free of noise related to patients who would have recovered without this new drug or treatment. Hence, the present invention also relates to a method for determining if a subject in severe sepsis with at least two organ failures or in septic shock with at least two organ failures is to be enrolled in a clinical trial for evaluating the efficiency of a pharmaceutical treatment for improving outcome for such a patient, comprising a step of establishing a prognosis for said subject by a method as above-described, wherein said subject is enrolled if the measured level of S100A8/A9 complex is above the predetermined threshold.

As a corollary of the above method, the invention also pertains to a method for testing the efficiency of a pharmaceutical treatment for improving outcome of severe syndromes with at least two organ failures, comprising the following steps:

(i) selecting a patient in severe sepsis with at least two organ failures or in septic shock with at least two organ failures, and determining the level of S100A8/A9 complex in a biological sample from said patient obtained before the beginning of said pharmaceutical treatment;

(ii) from at least another sample from said patient, obtained after the beginning of said pharmaceutical treatment, determining the level of S100A8/A9 complex;

(iii) comparing said obtained values;

wherein a decrease of S100A8/A9 complex level following the beginning of the pharmaceutical treatment indicates that said treatment has been beneficial to the patient and is likely to improve outcome of severe syndromes with at least two organ failures.

In a preferred embodiment of the above-method, step (i) is performed at day 0 after the onset of the second organ failure, and the selected patient preferably has a S100A8/A9 complex level above a predetermined threshold as defined above. In this latter case, the treatment will be considered as beneficial to the patient and most likely to improve outcome of severe syndromes with at least two organ failures if the S100A8/A9 complex level decreases below said threshold.

The skilled artisan can adapt this method for performing it with a follow-up of the patient based on the measure of S100A8 and/or S100A9 expression level instead of (or in addition to) the level of S100A8/A9 complex.

Another aspect of the present invention is a kit for performing any of the above-described methods based on the measure of the S100A8/A9 complex, comprising a molecule specifically binding to the S100A8/A9 complex and a notice of use explaining the predictive value of the plasma level of S100A8/A9 complex on the outcome of septic shock. The skilled artisan can choose any kind of specific binder, such as an antibody, and antibody fragment, an aptamer, a sugar etc., to put into such a kit, provided this binder can be used to measure the level of S100A8/A9 complex in an appropriate biological sample from a patient. In a preferred embodiment, the notice also provides a protocol description for measuring the S100A8/A9 complex level in a biological sample (for example, a plasma sample), as well as an indication of the threshold above which the level will be indicative of a bad prognosis for a patient. In an even more preferred embodiment, information concerning the sensitivity and specificity of the test which can be carried out with the kit will also be indicated in the notice, in relation with the threshold.

Of course, the kit according to the invention can also comprise other components selected amongst reagents for performing an immunoassay (buffers, enzymes, labeling molecules, etc.), quality controls, one or more calibrator(s), etc.

Other characteristics of the invention will also become apparent in the course of the description which follows of the biological assays which have been performed in the framework of the invention and which provide it with the required experimental support, without limiting its scope.

EXAMPLES

Example 1

S100A8/S100A9 Plasma Level at D0 is Indicative of Outcome of Patients in Septic Shock Materials and Methods All the experiments reported below have been carried out with the following materials and methods.

Patients

This multi-centre study was approved by the Cochin Hospital Ethics Committee (#CCPPRB 2061) and involved patients from four Intensive Care Units (two medical, two surgical). Only patients fulfilling the criteria of septic shock defined according to the ACCP/SCCM consensus conference (Bone et al., 1992) were screened. Inclusion criteria required patients in septic shock having at least two organ failures as defined by the SOFA (sequential organ failure assessment) score. Patients having at least a level strictly >2 for each organ failure were considered (Vincent et al., 1998; Vincent et al., 1996). The first blood sample was taken on day 0 (D0), defined as occurring within 24 hours of development of the second organ failure. A second sample, D1, was taken 24 hours later. Blood was taken for gene expression and for the plasma level of the S100A8/A9 complex.

Flow Cytometry for Monocyte HLA-DR Expression Measurement

Whole blood was incubated with appropriate antibodies conjugated with fluorochrome (Fluorescein isothiocyanate (FiTC) or Phycoerythrin (PE)): anti CD14-FiTC (clone RMO52, Beckman Coulter, Marseille, France) and PE conjugated irrelevant isotype control antibodies (Simultest control, BD Biosciences, San Jose, Calif., USA) or anti HLA-DR-PE (clone L243, BD Biosciences). Conversion of mean fluorescence intensities into the number of Antibody Bound per Cell (AB/C) was performed using QFCM (Quantitative Flow CytoMetry).

Plasma Cytokines Measurements

Plasma IL-10 (optEIA™ set; PharMingen, San Diego, Calif., USA), IL-12p40 and MIF (R&D Systems, Abingdon, Oxon, UK) concentrations were determined by an immunoenzymatic method (ELISA) according to the manufacturer's recommendations. Standard samples ranged from 7·8 to 500 pg/ml for IL-10, and from 31·25 to 2000 pg/ml for IL-12p40 and MIF. Detection thresholds were 2·7±3·1 pg/ml for IL-10, 25·8±33·3 pg/ml for IL-12p40 and 25·7±34·6 pg/ml for MIF.

Plasma S100A8/A9 Complex Level

The technique was adapted from a previous publication (Ikemoto et al., 2003) using blood taken from 34 healthy subjects, paired by age and sex. Levels averaged 0.26 microg/ml with a range 0.052-0.468 µg/ml. Briefly, 100 µl of diluent solution were added to each well of a 96-well polycarbonate plate coated with the first antibody (Mo2B9; 0.166 mg/L). Plasma samples, previously diluted with a working Block-Ace™ (Dainippon Pharmacology Co Ltd) solution or the MRP8/14 complex calibrator solution, were then added and the plate was mixed for 15 seconds. The plate was then incubated for 1 hr to allow the immunological reaction to proceed. After the plate was washed 5 times, 100 µl of F(ab')2-biotin conjugate (second antibody Mo3D2 in the working Block-Ace™ solution containing 0·5 g/L thimerosa) were added and the plate incubated for a further 1 hour. After washing the plate as above, 100 µl of streptavidin-HRP conjugate diluted 1500-fold with the working Block-Ace solution were added and the plate was incubated for 30 min. Finally, HRP activity was determined by colorimetry. Within-run CVs were 3·9-5·6%, between-day CVs were 5·9-7·6%, and mean recovery was 98% (range 85-103%).

S100A8-A9 Gene Expression by Quantitative RT-PCR

RNA samples were obtained at D0 and D1 after elimination of mature PMNs by gradient centrifugation (Ficoll). Cell analysis included morphological characteristics by light scatter and CD66b expression (FACScalibur) for evaluating the proportion of immature cells (granulocyte lineage) ((Payen et al., 2008)). At D0 and D1, the proportion of myeloid cells was almost 50% of the separated cells. That implies that remaining mononuclear cells such as lymphocytes and monocytes were around 50%. Total RNA was extracted using the Rneasy kit (Qiagen) and samples were treated with Rnase-free DNAse I. The quality and quantity were estimated on the bioanalyzer (Agilent) and quantities of total RNA were confirmed on a Nanodrop spectrophotometer. qRT-PCR were performed for S100A8 and S100A9 according to the manufacturer's specifications (Applied Biosystems, Foster City, Calif., USA, table 1)), compared to an endogenous control eukaryotic 18S rRNA. Results are expressed in Delta Ct (concentration threshold): CtS100Ax-Ct18S.

TABLE 1

Characteristics of Gene expression Assays for Real-Time PCR. Assays are designed and distributed by Applied Biosystems

| Gene Symbol | Gene Name | NCBI Gene ref | Assay ID |
| --- | --- | --- | --- |
| 18S | Eukaryotic 18S rRNA | X03205.1 | Hs99999901_s1 |
| S100A8, MRP8 | S100 calcium binding protein A8 | NM_002964.3 | Hs00374264_g1 |
| S100A9, MRP14 | S100 calcium binding protein A9 | NM_002965.3 | Hs00610058_m1 |

Statistics

Quantitative results are expressed in median±Inter Quartile Range (IQR). Comparison of quantitative variables was done with a Mann-Whitney test and qualitative variable by chi-squared testing. Correlation studies were performed by the Spearman correlation test. A p-value<0·05 was considered as statistically significant. Based on the few data on human septic shock previously published (Payen et al., 2008), the inventors assumed an expected mortality of 40% in septic shock patients (Annane et al., 2007; Sprung et al., 2008), and a difference, between survivors and non-survivors, in S100A8/A9 complex of 2 µg/ml, with a standard error of 2.35 (Payen et al., 2008). Accordingly, a sample size of 47 patients had to be recruited, controlling for a type I error probability at 0.05 and a power of 0.80.

Results

Forty nine patients were included and their clinical characteristics are summarized in table 2 below. Surviving Sepsis Campaign guidelines for patient management were followed (Dellinger et al., 2004). On day 1, 9 patients received activated Protein C (18%) and 35 were treated by hydrocortisone (71%). Thirty one patients had undergone a recent (<2 days) surgical procedure. Fifteen patients died within the 28-day study period. Twelve patients died during the first 7 days, with 5 deaths within D0 and D2 due to multiple organ failure related to the episode of septic shock. The three patients who died after Day 7 (1 at D24 and 2 at D26) did so because of non-treatable respiratory failure and severe hypoxaemia, delayed multiple organ failure, and a moribund condition mandating treatment limitation. At D0, the SAPSII clinical severity score differed between survivors and non-survivors whereas the SOFA score was not significantly different (table 2).

TABLE 2 clinical characteristics, type of sepsis, and cardiovascular support at day 0 in total, alive and dead patients.

|  | Total n = 49 | Alive n = 34 | Dead n = 15 | P |
|---|---|---|---|---|
| Age (y/o) | 64 (24) | 62 (18) | 75 (17) | 0.0040 |
| Sex M/F | 34/15 | 24/10 | 10/5 | NS |
| SAPSII | 57 (20) | 52 (18) | 70 (19) | <0.0001 |
| SOFA D0 | 10 (4) | 10 (3) | 11 (4) | NS |
| nbre Organ Failure | 3 (1) | 3 (1) | 4 (2) | 0.0215 |
| Postoperative | 31/18 | 21/13 | 10/5 | NS |
| Infection site: | | | | |
| thorax | 10 | 7 | 3 | |
| Abdomen | 24 | 15 | 9 | |
| Urinary tract | 7 | 6 | 1 | |
| CNS | 1 | 0 | 1 | |
| peripheral | 7 | 6 | 1 | |
| Treatments: | | | | |
| Catecholamines (μg/kg/min): | | | | |
| Norepinephrine (n = 45) | 0.4 (0.5) | 0.3 (0.4) | 0.7 (1) | 0.0100 |
| Epinephrine (n = 8) | 0.2 (0.7) | 0.4 (0.7) | 0.2 (0.5) | NS |
| Dobutamine (n = 7) | 10.0 (12.5) | 5 (0) | 15 (10) | 0.0528 |
| Dopamine (n = 1) | 10 (0) | 10 (0) | — | — |
| Hydrocortisone Hemisuccinate (n) | 35 | 21 | 14 | |
| Activated protein C | 9 | 4 | 5 | |

Blood inflammatory mediator results are summarized in table 3. There was no difference at day 0 for either plasma levels of IL-10 or IL-12p40, or HLA-DR monocyte expression between survivors and nonsurvivors. Plasma MIF levels were significantly higher in patients who eventually died (p<0.003), however there was a large overlap in values between the two groups.

TABLE 3 cytokine plasma levels or monocyte expression of HLA-DR at day 0.

|  | Total n = 49 | Alive n = 34 | Dead n = 15 | p |
|---|---|---|---|---|
| HLA-DR (AB/C) | 2797 (3097) | 2826 (3683) | 2762 (2822) | NS |
| IL-10 (pg/ml) | 308 (909) | 246 (686) | 514 (999) | NS |
| IL-12p40 (pg/ml) | 15 (111) | 29 (109) | 12 (136) | NS |
| MIF (pg/ml) | 1603 (8531) | 1005 (3642) | 9049 (17490) | 0.0033 |

MIF: macrophage migration inhibiting factor.

S100A8/S100A9 Complex Plasma Protein and mRNA Levels

At D0, plasma levels of the S100 A8/A9 complex were markedly different between eventual survivors and non-survivors (3.7 μg/ml (IQR: 0.9) vs 13.3 μg/ml (IQR: 5.4 p<0.0001). There was no overlap between the 2 groups. Similar results were observed at day1. (FIG. 1). As a consequence, specificity and sensitivity of 100% were obtained, with a threshold plasma level for mortality risk of 8.1 μg/ml. Importantly, this was not influenced by the number of organ failures measured on day 0. Survivors with 2 organ failures and those having >2 organ failures at day 0 had similar plasma levels (3.5 μg/ml IQ 1.4 (n=8) vs 3.7 μg/ml IQ 0.9 (n=25)). The validity of such a prognostic marker was verified by looking at patients receiving activated Protein C (aPC) and/or hydrocortisone. Of the nine patients (18%) receiving aPC after day 0, five survived (D0 levels: 3.4 μg/ml; IQR 1.1) and 4 died (D0 levels: 15.7 μg/ml IQR 3.6). Likewise, D0 levels in patients treated subsequently with corticosteroids (35 patients) were 3.7 μg/ml (IQR 10) in survivors vs 13.8 μg/ml (IQR 5.6) in eventual non-survivors. The dosage requirement of catecholamines (norepinephrine and dobutamine) was higher in eventual non-survivors (p<0.01) (table 1).

Figure 2:
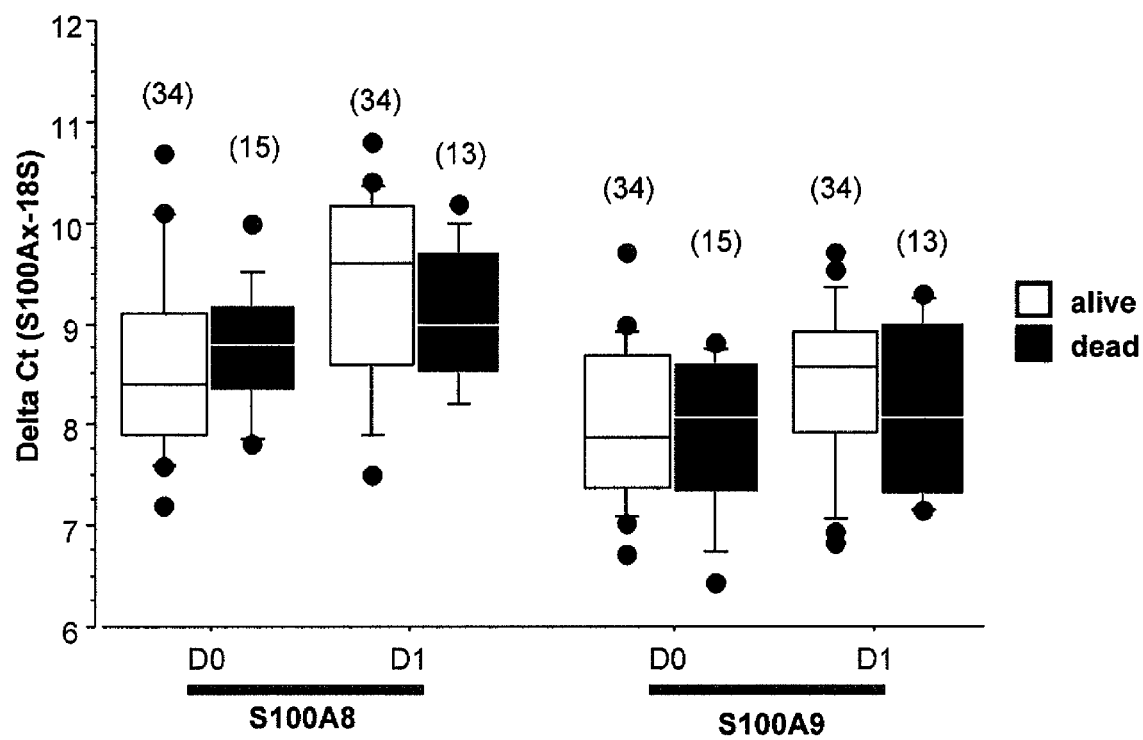
FIG. 2: shows the S100 A8 (left part) and A9 (right part) RT-PCR gene expression in circulating white cells. White box represented survivors and black box the non survivors. Box plot represents the median with the 25 and 75 percentiles, the bar corresponded to the 10th and 90th percentiles. Dots are the values lower than 10th percentile or over the 90th percentile. Statistics were performed with Mann Whitney non parametric test.
Figure 3:
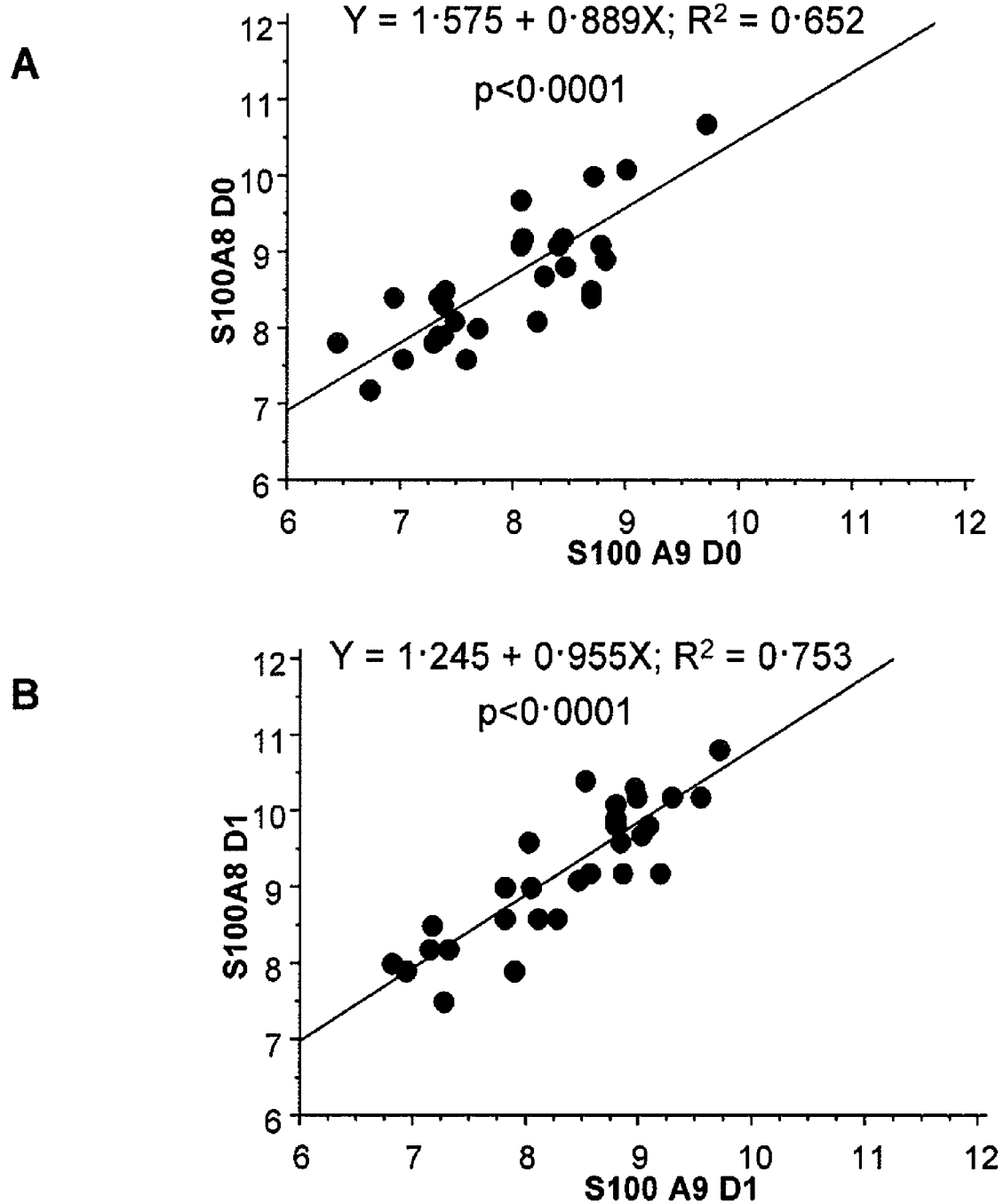
FIG. 3: shows the correlation between S100A8 and S100A9 gene expression in RT-PCR. The correlation was performed with the Spearman test.

The mRNA levels for S100A8 or S100A9 genes in circulating monocytes did not differ between survivors and non survivors on either day 0 or day 1 (FIGS. 2A and B). Gene expression for S100A8 and S100A9 correlated well together (r=0.81 at D0 and r=0.87 at D1, p<0.0001 FIG. 3), however no correlation was seen with plasma S100A8/A9 complex levels on either D0 or D1 (data not shown).

Discussion:

This multicentre study on septic shock with at least 2 organ failures demonstrates the outcome predictive value of the plasma level of S100A8/9 complex at day 0 of the occurrence of the $2^{nd}$ organ failure. The survivals had a plasma level of the complex S100A8/A9 13 times higher than normal values, which differed largely from dead patients. Such a difference was independent of the number of organ failures at day 0 or the subsequent use of aPC or GCst. This difference was stable at least during the first 2 days, with a threshold of risk of death at 8.1 μg/ml. The plasma protein level difference did not correlate with S100A8 and A9 gene expression on peripheral white blood cells, suggesting at the early phase other origins for this complex than circulating immune cells. The calculated threshold for risk of death (8.1 μg/ml) should be tested in a larger cohort of patients, and possibly more accurately re-evaluated.

Need for a prognostic marker in septic shock is justified by several concerns. Knowing rapidly the individual high risk of death might help clinicians to better select patients requiring expensive and sophisticated new future drugs or strategies, to limit the waste of money for patients who will recover after "classic" resuscitation. The other advantage might be a better selection of patients to enrol in future clinical trials aiming outcome improvement.

Ideal prognostic marker in septic shock has to be: specific and sensitive for outcome prediction; stable during a compatible time for clinical interpretation (1 or 2 days); easily measured in plasma; exclusively dependent on outcome and not on effectiveness of subsequent treatments; and relatively inexpensive. The observed results fulfil the above-mentioned criteria. Although limited in size, this multicentric studied cohort seems valid for clinicians, since it contained medical and surgical sepsis with a calibrated severity at inclusion, receiving a large proportion of aPC and GCst, with no patient exclusion. In addition, the plasma levels in survivors corresponded well with previous results in acute arthritis or in inflammatory aetiologies (Foell et al., 2004; Sampson et al., 2002).

Apart from scores such as SAPS II or APACHE II or SOFA, which requires 24 hours evolution to be computed, several early biological markers have been tested to predict mortality in severe sepsis and septic shock. Most of the known parameters can only reflect some subsystems or time-dependent aspects of sepsis, with few data focused on calibrated septic shock severity and organ failure. If procalcitonin (PCT) could be sensitive enough to diagnose a systemic inflammation related to bacterial infection, only one study addressed the potential of PCT as a prognostic marker in septic shock (Clec'h et al., 2004). Plasma PCT levels at day 1 were significantly higher in non survivals compared to survivors, with 87.5% sensitivity and a poor 45% specificity. IL-6, a marker of the severity of systemic inflammation in septic shock, might help to select the patients to be enrolled in trials (Abraham et al., 2001), but cannot be used as an outcome predictor. The most recent data on early HLA-DR measurements on circulating monocytes were shown poorly predict septic shock outcome (Monneret et al., 2006). Testing of BNP plasma values during the first 3 days of severe sepsis or septic shock (Varpula et al., 2007) showed a large overlapping between survival and non survival values, especially in the septic shock sub-population. The measurements of the plasma soluble TREM in septic patients including septic shock (Gibot et al., 2005) had a relatively low sensitivity for outcome prediction, which precluded its use as a prognostic marker alone. Recently, Scherpereel et al. demonstrated preliminary results on endocan, a circulating proteoglycan (Scherpereel et al., 2006). The large overlap between values in survivors and non-survivors need more clinical evaluation.

In a recently published study (Bopp et al., 2008), the plasma sRAGE concentration was tested as a prognostic marker in septic patients. If plasma sRAGE in nonsurvivor was higher than in survivors with a specificity of 75% and a sensitivity of 84.6%, no information on septic shock was mentioned. If these receptors are sensing not only pathogen-associated molecular patterns (PAMPs) but also endogenous DAMPs, S100 proteins family may play an important role (Foell et al., 2007).

The first members of the S100 protein family were discovered more than 40 years ago and to date, more than 20 members of this protein family have been described (Ravasi et al., 2004). Three S100 proteins (S100A8, A9, and A12) are specifically linked to innate immune functions. S100A8 and S100A9 are found in granulocytes, monocytes and early differentiation stages of macrophages (Foell et al., 2007). In contrast, S100A 12 (extracellular newly identified RAGE binding protein, EN-RAGE) is more restricted to granulocytes (Vogl et al., 1999). There is evidence that these phagocyte-specific S100 proteins are actively secreted via an alternative pathway bypassing the classical Golgi-route (Rammes et al., 1997). This mode of secretion that is typical for DAMP-related factors, which have a role in cell homeostasis as intracellular molecules but turn into proinflammatory danger signals after release to the extracellular compartment due to cell damage, infections, or inflammation. Such a concept may then explain why the plasma level is dramatically higher in patients who will not survive, suggesting a more severe lost of cell homeostasis.

Among the extracellular functions, some are related to anti-infectious host defense mechanisms related to proinflammatory mechanisms. Noncovalently associated S100A8/S100A9 complexes are secreted in inflammation by activated phagocytes in contact with inflamed endothelium with a strong correlation of their plasma concentrations to inflammation (Foell et al., 2004). The studied population was homogenous in term of severity and cannot be clinically distinguished for survivors and non survivors at day 0. Except for MIF plasma levels, the measured markers of inflammation at day 0 were also similar between survivors and non survivors. The large difference in S100A8/A9 complex at day 0 between survivors and non survivors associated with a higher SAPS II confirms the relation between S100A8/A9 complex and the severity of inflammation. As a consequence, such a complex might be more sensitive and specific to characterize the inflammation severity than the other studied markers.

Release of S100A8 and S100A9 is independent from de novo synthesis and is rather associated with down-regulation of mRNA expression of both genes (Foell et al., 2007). The absence of correlation at day 0 between the plasma level of the complex S100A8/A9 and white cell S100A8 and A9 gene expression confirms the absence of an early de novo synthesis. This may also suggest that extracellular signalling via S100A8/S100A9 is restricted to early differentiation stages of monocytes/macrophages or other myeloid cells or to other cells origins such as endothelial cells. The large difference between survivals and non survivals cannot be compared with other published results in septic shock. However, the survival group had plasma levels of S100A8/A9 complex that fitted well with previous publications in acute arthritis (Foell et al., 2004), chronic inflammatory bowel disease, and systemic auto-immune disease. In our knowledge, only during acute rejection of transplanted kidney similar plasma levels than those found in non survivors have been reported (Jung et al., 2008). Although not useful to predict the kidney rejection versus non viral inflammation, such elevated plasma level related well with the inflammatory intensity.

The recently published study on mice sepsis (Vogl et al., 2007)(LPS injection or caecal ligature and puncture) demonstrates a major role of S100A8 and A9 on sepsis mechanisms. Mice lacking S100A8-A9 complexes were protected from *Escherichia coli*- or endotoxin-induced lethal shock. The complex S100A8/A9 amplified the endotoxin-triggered inflammatory responses of phagocytes such as: intracellular translocation of myeloid differentiation primary response protein 88 and activation of interleukin-1 receptor-associated kinase-1 and nuclear factor-kB, resulting in elevated expression of tumor necrosis factor-α (TNF-α). Using phagocytes expressing a nonfunctional Toll-like receptor 4, the authors have demonstrated that S100A8 specifically interacts with the TLR4-MD2 complex, thus representing an endogenous ligand of TLR4.

The limit of this study might be related to the relatively small size of the population. However, the statistical power computation based on previous results on mortality and on S100A8/A9 levels (Payen et al., 2008) fitted well with the size of the present population. The found large difference between survivals and non-survivals at day 0, despite the multicentric recruitment of patients, having different types of infections, medical and surgical context, with subsequent activated protein C and/or cortico-steroids treatment, suggests a very robust value of this marker for prognosis. The other limit may relate to the marker release origin, since plasma milieu integrated all the potential cellular sources, whereas the gene expression concerned only the studied cells, i.e. blood monocytes and immature myeloid cells. The later cells can be the larger proportion of cells at day 0 after removing mature PMNs. This could be an advantage for the S100A8/A9 complex, since it might be released by those cells, supposed to contain large quantities of this complex (Foell et al., 2007).

In conclusion, this report is the first on plasma levels of the complex S100A8/A9 in septic shock with at least two organ failures. The demonstration of the good prognostic value of such a complex to predict outcome in septic shock patients may open a new area for the rapid determination of patients who have to be treated with the most expensive drugs, and/or who have to be enrolled for future clinical trials based on outcome benefit.

Example 2

Gene Profiling in Human Blood Leukocytes During Recovery from Septic Shock

Material and Methods

Patients: the study concerned patients in septic shock as defined by the ACCP/SCCM consensus and was approved by the Cochin Hospital Ethics Committee (#CCPPRB 2061). Patients over 18 y/o were included after written informed consent from their next of kin. Inclusion criteria were: a documented infection by clinical and/or bacteriological evidence; and septic shock (cardiovascular failure with norepinephrine) with at least one additional sepsis-related organ failure. Exclusion criteria were: long lasting glucocorticosteroid treatment; recent treatment for cancer, immune or hematologic diseases and a life expectancy <6 months. Blood samples were initiated within 48 hours after reaching the inclusion criteria (D0) and at days 1 (D1), 7 (D7), and 28 (D28). 28-day outcome (dead or alive) was also recorded.

Microarray procedure: Mature granulocytes were eliminated from blood by gradient centrifugation (Histopaque, Sigma, St Quentin Fallavier, France). Collected cell analysis included morphological characteristics by light scatter and CD66b expression (FACScalibur, BD Bioscience, Le Pont de Claix, France) for evaluating the proportion of immature cells (granulocyte lineage). Accordingly, the studied cells were at D0 and D1 myeloid cell for 50% and circulating immune mononuclear cells (lymphocytes and monocytes) for the remaining, which became up to 98% at D7 and D28.

Total RNA was extracted using the Qiagen Rneasy Mini kit (Qiagen). All RNA samples were treated with Rnase-free DNAse I during the extraction as a step of the extraction protocol. The quality was estimated on the bioanalyzer (Agilent) and quantity of total RNA was measured on Nanodrop spectrophotometer (Labtech International). Fifteen micrograms of total RNA were processed for microarray analysis. Double-strand cDNA was obtained by the reverse transcription using Superscript II reverse transcriptase (Invitrogen) according to the manufacturer's instructions.

Hybridization was performed on the slide Lab-Arraytor® human 500-1 cDNA (SIRS-Lab GmbH, Jena; Germany). Description of the slide (GPL1936), experimental design and tables of the normalized data for outcome and time evolution, were registered in the Gene Expression Omnibus database under the accession numbers GSE5262 and GSE5271. Minimum Information Microarray Experiment (MIAME) criteria have been carefully fulfilled.

Data measurement: Unpaired t-test was used to generate the list of genes with different levels of expression according to outcome, and Anova analysis for comparisons over time. $p<0.05$ was considered as statistically significant.

Validation of gene expression by Real-Time quantitative PCR (RT-qPCR): 4 genes have been selected for validation on the basis of their fold change having a stable trend over time. In addition, their scattering values allowed to well assess a potential correlation. Reverse transcription reactions (High Capacity cDNA Archive kit, Applied Biosystems, Foster City, Calif., USA) and TaqMan Gene Expression Assays on ABI PRISM 5700 Sequence Detection System (Applied Biosystems) were performed according to the manufacturer's specifications. Eukaryotic 18S rRNA was used as an endogenous control and the reference standard sample was Universal Human Reference RNA (Clontech).

Results:

The median age of the population was 59 y.o (IQR 16) with a median SAPS II 50 (IQR 14), a number of organ failure of 3 (IQR 1) and a Sepsis Related Multiple Organ Failure Score (SOFA) score of 10 (IQR 3) at D0. Three patients (17%) died all within the first week of the study.

Gene expression in leukocytes over 28 days in survivors (n=14)

Ten genes demonstrated significant expression variations over time in comparison with D0 (p<0.05) (table 4). CD74 implicated in antigen presentation increased its expression over time until D28. By contrast, the expression of genes encoding pro-inflammatory proteins such as S100 A8, A12, arachidonate pathway (ALOX5AP) and the isoform alpha of IL-3 growth factor receptor all decreased their expression over time. Table 5 summarizes the variations (fold changes (Dx/D0)) at each time for each gene of interest.

TABLE 4 list of the genes of interest for sepsis recovery

| Reference ID SIRS-lab | Gene ID | Description | Category of function |
|---|---|---|---|
| 1 AK055068 | TPD52L2 | tumor protein D52-like 2 | Cell proliferation |
| 2 XM_086400 | S100A8 | S100 calcium binding protein A8 (calgranulin A) | Cell cycle progression and differentiation |
| 3 D49410 | IL3RA | interleukin 3 receptor, alpha (low affinity) | Cell surface receptor of hematopoietic growth factor |
| 4 NM_006084 | ISTF3G | interferon-stimulated transcription factor 3, gamma | Transcription factor |
| 5 XM_001682 | S100A12 | S100 calcium binding protein A12 (calgranulin C) | antimicrobial activity |
| 6 XM_015396 | ALOX5AP | arachidonate 5-lipoxygenase-activating protein | leucotrienes synthesis |
| 7 XM_003937 | CD74 | CD74 antigen | invariant polypeptide of MHC class II antigen-associated |

TABLE 4-continued list of the genes of interest for sepsis recovery

| Reference ID SIRS-lab | Gene ID | Description | Category of function |
|---|---|---|---|
| 8 XM_008570 | VAMP2 | vesicle-associated membrane protein 2 (synaptobrevin 2) | regulation of exocytosis |
| 9 XM_034770 | PAFAH1B1 | platelet-activating factor acetylhydrolase, isoform Ib, alpha subunit | inactivation of proinflammatory PAF |
| 10 XM 056009 | IGLL1 | immunoglobulin lambda-like polypeptide 1 | Immunoglobulin |

TABLE 5

Fold changes (FC Dx/D0) of selected genes for shock recovery at each time, expressed in mean ± SD

|  | D1/D0 | D7/D0 | D28/D0 |
|---|---|---|---|
| ALOX5AP | 1.80 ± 3.30 | 0.68 ± 0.58 | 0.36 ± 0.16 |
| CD74 | 1.46 ± 0.81 | 2.66 ± 1.54 | 4.14 ± 2.24 |
| IGLL1 | 1.45 ± 0.97 | 6.75 ± 9.05 | 1.99 ± 2.24 |
| IL3RA | 1.96 ± 1.54 | 1.00 ± 0.43 | 0.92 ± 0.30 |
| ISGF3G | 0.97 ± 0.50 | 1.23 ± 0.73 | 1.34 ± 0.65 |
| PAFAH1B1 | 0.97 ± 0.57 | 0.78 ± 0.52 | 1.41 ± 0.95 |
| S100A12 | 1.34 ± 0.88 | 0.60 ± 0.47 | 0.27 ± 0.19 |
| S100A8 | 1.04 ± 0.63 | 0.42 ± 0.50 | 0.17 ± 0.20 |
| TPD52L2 | 1.06 ± 0.45 | 0.77 ± 0.33 | 0.79 ± 0.30 |
| VAMP2 | 1.52 ± 1.36 | 1.54 ± 1.62 | 1.73 ± 0.80 |

Comparison Between Microarray and RT-qPCR Data in Survivors

The Real-Time PCR data correlated with microarray data for CD74, S100A8, S100A12 and VAMP2 expression (r=0.62 p<0.001, r=0.58 p<0.001, i=0.81 p<0.001 and 1=0.41 p<0.05 respectively.

The invention claimed is:

1. A method for in vitro establishing a prognosis for a subject in severe sepsis with at least two organ failures or in septic shock with at least two organ failures, consisting of the following steps:
   (i) from a plasma sample from said subject, measuring the level of S100A8/A9 complex in said sample, by immunoassay;
   (ii) comparing said level to a predetermined threshold plasma level of S100A8/A9 complex indicative for risk of death,
   wherein: if the level of S100A8/A9 complex in the plasma sample is above said predetermined threshold, the prognosis is that the subject will not survive said severe sepsis or said septic shock; and if the level of S100A8/A9 complex in the plasma sample is below said predetermined threshold, the prognosis is that the subject will survive said severe sepsis or said septic shock.

2. The method of claim 1, wherein said plasma sample has been collected at day 0, day 1 or day 2 after the onset of the second organ failure.

3. The method of claim 1, wherein said immunoassay is performed with an antibody which specifically binds to the S100A8/A9 complex.

4. The method of claim 3, wherein said antibody is fluorescently labeled.

5. The method of claim 1, wherein said immunoassay is an enzyme-linked immunosorbent assay (ELISA).

* * * * *